US00PP09018P

United States Patent [19]

Olesen et al.

[11] Patent Number: Plant 9,018

[45] Date of Patent: Dec. 20, 1994

[54] MINIATURE ROSE PLANT NAMED POULORAL

[75] Inventors: Mogens N. Olesen; Pernille Olesen, both of Fredensborg, Denmark

[73] Assignee: Bear Creek Gardens, Inc., Medford, Oreg.

[21] Appl. No.: 209,844

[22] Filed: Mar. 11, 1994

[51] Int. Cl.[5] ..... A01H 5/00

[52] U.S. Cl. ..... Plt./10.1

[58] Field of Search ..... Plt. 7.1, 10.1, 9, 10

*Primary Examiner*—Howard J. Locker

*Attorney, Agent, or Firm*—Klarquist Sparkman Campbell Leigh & Whinston

[57] ABSTRACT

A miniature rose plant having a compact, dwarf growth habit; ease of propagation from softwood cuttings; attractive coral flower color; long shelf life, the flowers staying on the plant in an attractive state for up to two weeks; and resistance to disease.

1 Drawing Sheet

The present invention relates to a new and distinct variety of rose plant of the miniature class which was originated by us by crossing an unnamed seedling with the variety RUImired, U.S. Plant Pat. No. 5,770.

The primary objective of this breeding was to produce a new rose variety having a compact, dwarf plant habit; a clean, bright, coral orange color; ease of propagation from softwood cuttings; resistance to disease; and good shelf life as a pot rose. The objective was substantially achieved, along with other desirable improvements, as evidenced by the following unique combination of characteristics that are outstanding in the new variety and that distinguish it from its parents, as well as from all other varieties of which we are aware:

1. Attractive coral flower color;
2. Good shelf life as a potted rose;
3. Ease of propagation from softwood cuttings;
4. Compact, dwarf plant habit; and
5. Resistance to powdery mildew and rust.

Asexual reproduction of this new variety by softwood cuttings as performed at Wasco and Somis, Calif., and Fredensborg, Denmark, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color descriptions using terminology in accordance with the Royal Horticultural Society (London) Colour Chart, except where ordinary dictionary significance of color is indicated.

Parentage:

*Seed parent.*—Unnamed seedling.

*Pollen parent.*—RUImired.

Classification:

*Botanical.*—*Rosa hybrida.*

*Commercial.*—Miniature.

FLOWER

Observations made from specimens grown in greenhouse environments at Somis, Calif., and Fredensborg, Denmark.

Blooming habit: Recurrent.

Bud:

*Size.*—1.3 cm long when the petals start to unfurl.

*Form.*—The bud form is short, pointed ovoid.

*Color.*—When sepals first divide, bud color is Red Group 41C. When half brown, the upper sides of the petals are Red Group 41C, and the lower sides of the petals are Red Group 43C.

*Sepals.*—Color: Green Group 138A. Surface Texture: Covered in fine hairs. These are three normally appendaged sepals. These are two unappendaged sepals with hairy edges.

*Receptacle.*—Color: Green Group 141C. Shape: Funnel. Size: Small (6 mm×3 mm); slender. Surface: Smooth.

*Peduncle.*—Length: Short (4 cm to 5 cm). Surface: Smooth. Color: Medium green. Strength: Stiff, erect, slender.

Bloom:

*Size.*—Small. Average open size is 4 cm.

*Borne.*—Singly and several together, in pyramidal to rounded clusters of 3 to 5 flowers.

*Stems.*—Short (13 to 15 cm); strong.

*Form.*—When first open: High centered. Permanence: Flattens, all petals curl, quill fashion.

*Petalage.*—Number of petals under normal conditions: 30 to 40.

*Color.*—The upper sides of the petals are Red Group 41C. The reverse sides of the petals are Red Group 43C. The base of each petal has a small, Yellow Group 4C half-moon at the point of attachment. The major color on the upper side is Red Group 41C.

*Variegations.*—None.

*Discolorations.*—The general tonality at the end of the first and third days: No change.

*Fragrance.*—Slight.

Petals:

*Texture.*—Thin.

*Shape.*—Oval.

*Form.*—Tips slightly recurved, edges slightly quilled.

*Arrangement.*—Imbricated, with few petaloids in the center.

*Persistence.*—Drop off cleanly.

*Lastingness.*—On the plant: Very long (14 to 16 days). As a cut flower: Very long (10 to 12 days).

Reproductive parts:

*Anthers:*—Size: Small. Quantity: Few. Color: Yellow. Arrangement: Regular around styles, mixed with petaloids.

*Filaments.*—Color: White.

*Pollen.*—Color: Lemon yellow.

*Styles.*—Color: White.

*Stigmas.*—Color: Red.

Form: Bush.

Growth: Vigorous, dwarf, upright, branching. Plant is 36 to 41 cm tall by 25 cm wide.

Foliage:

*Number of leaflets on normal mid-stem leaves.*—5.

*Size.*—Small (5 cm×4 cm).

*Quantity.*—Normal.

*Color.*—New foliage: Green Group 143A. Old foliage: Green Group 137A.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Smooth, with occasional prickles.

*Stipules.*—Short, bearded.

*Disease resistance.*—Resistant to mildew and rust under normal growing conditions at Somis, Calif.

Wood:

*New wood.*—Color: Light Green. Bark: Smooth.

*Old wood.*—Color: Green. Bark: Smooth.

Prickles:

*Quantity.*—On main canes from base: Few. On laterals from main canes: Few.

*Form.*—Short (3 mm), straight.

*Color when young.*—Transparent.

Small prickles:

*Quantity.*—On main stalks: None. On laterals: None.

We claim:

1. A new and distinct variety of rose plant of the miniature class, substantially as herein shown and described, characterized particularly as to novelty by the unique combination of its compact, dwarf growth habit; ease of propagation from softwood cuttings; attractive coral flower color; long shelf life, the flowers remaining on the plant in an attractive state for up to two weeks; and resistance to disease.

* * * * *

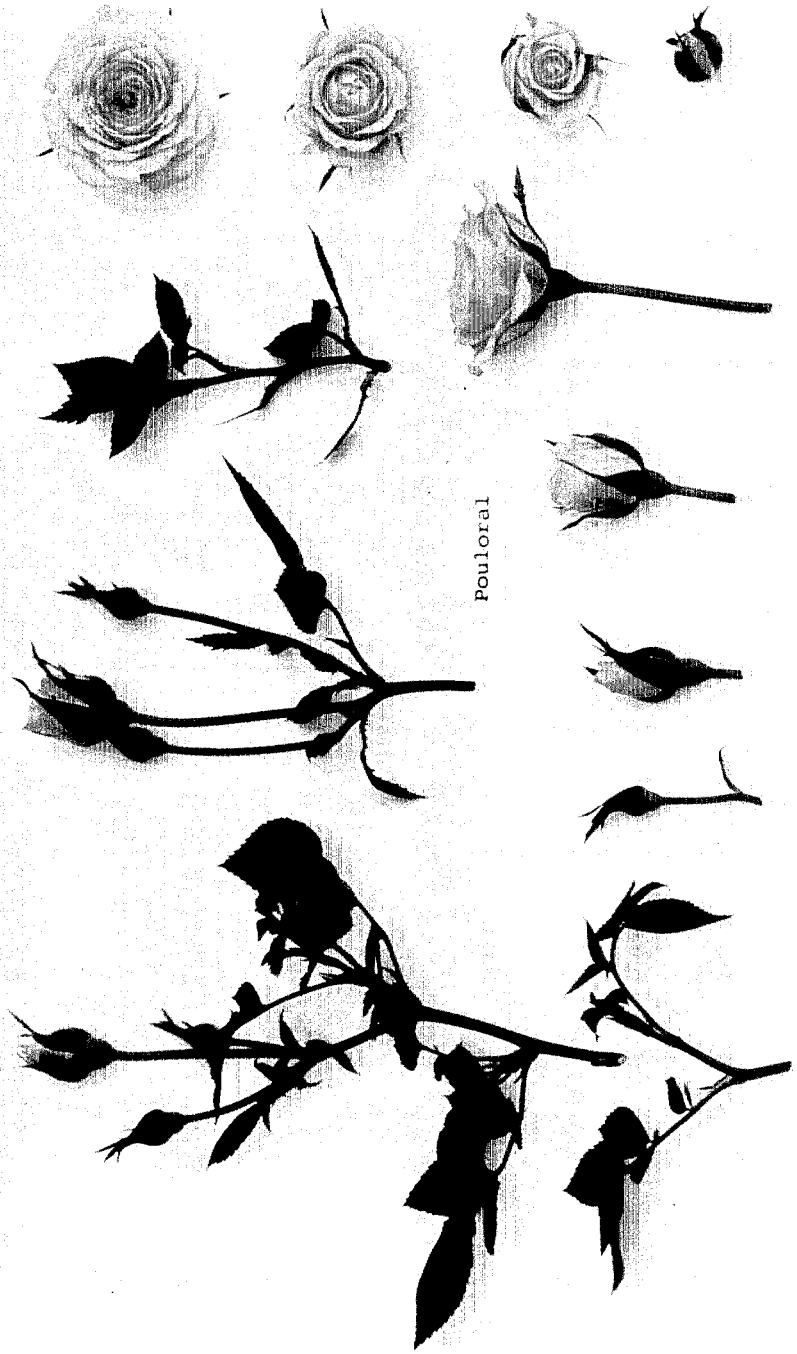
Pouloral